(12) United States Patent
Inoue et al.

(10) Patent No.: US 12,031,016 B2
(45) Date of Patent: Jul. 9, 2024

(54) DISPERSION COMPOSITION CONTAINING CARBOXYMETHYL CELLULOSE

(71) Applicant: NIPPON PAPER INDUSTRIES CO., LTD., Tokyo (JP)

(72) Inventors: Kazuhiko Inoue, Tokyo (JP); Hiroyoshi Suzuki, Tokyo (JP); Kasumi Nishigaya, Tokyo (JP); Takeshi Nakatani, Tokyo (JP)

(73) Assignee: NIPPON PAPER INDUSTRIES CO., LTD., Tokyo (JP)

( * ) Notice: Subject to any disclaimer, the term of this patent is extended or adjusted under 35 U.S.C. 154(b) by 733 days.

(21) Appl. No.: 17/056,291

(22) PCT Filed: May 17, 2019

(86) PCT No.: PCT/JP2019/019675
§ 371 (c)(1),
(2) Date: Nov. 17, 2020

(87) PCT Pub. No.: WO2019/221273
PCT Pub. Date: Nov. 21, 2019

(65) Prior Publication Data
US 2021/0253831 A1 Aug. 19, 2021

(30) Foreign Application Priority Data
May 18, 2018 (JP) .................. 2018-096479
Sep. 27, 2018 (JP) .................. 2018-182110

(51) Int. Cl.
| | |
|---|---|
| *C08L 1/28* | (2006.01) |
| *A23K 20/163* | (2016.01) |
| *A23L 2/52* | (2006.01) |
| *A23L 29/262* | (2016.01) |
| *A61K 8/04* | (2006.01) |
| *A61K 8/73* | (2006.01) |
| *A61K 9/10* | (2006.01) |
| *A61K 47/38* | (2006.01) |
| *A61Q 19/00* | (2006.01) |
| *C08J 3/07* | (2006.01) |
| *C09D 7/43* | (2018.01) |
| *D21H 17/26* | (2006.01) |

(52) U.S. Cl.
CPC ............ *C08L 1/286* (2013.01); *A23K 20/163* (2016.05); *A23L 2/52* (2013.01); *A23L 29/262* (2016.08); *A61K 8/04* (2013.01); *A61K 8/731* (2013.01); *A61K 9/10* (2013.01); *A61K 47/38* (2013.01); *A61Q 19/007* (2013.01); *C08J 3/07* (2013.01); *C09D 7/43* (2018.01); *D21H 17/26* (2013.01); *A23V 2002/00* (2013.01); *A61K 2800/48* (2013.01); *C08L 2201/54* (2013.01)

(58) Field of Classification Search
CPC ......................................................... C08L 1/286
See application file for complete search history.

(56) References Cited

U.S. PATENT DOCUMENTS

| | | | | |
|---|---|---|---|---|
| 5,527,902 A | * | 6/1996 | Loth | ................. B01J 20/28047 |
| | | | | 536/87 |
| 2019/0055323 A1 | | 2/2019 | Kakubari et al. | |
| 2019/0116858 A1 | | 4/2019 | Kawasaki et al. | |
| 2021/0079173 A1 | | 3/2021 | Inoue et al. | |

FOREIGN PATENT DOCUMENTS

| | | | |
|---|---|---|---|
| EP | 582474 A1 * | 2/1994 | ........... A01G 9/1086 |
| EP | 0582474 B1 | 10/1996 | |
| JP | 10-251119 A | 9/1998 | |
| JP | 10-251301 A | 9/1998 | |
| JP | 10-251446 A | 9/1998 | |
| JP | 10251301 A * | 9/1998 | |
| JP | 11-140793 A | 5/1999 | |
| JP | 2000-034301 A | 2/2000 | |
| JP | 2002-194001 A | 7/2002 | |
| JP | 2007-191558 A | 8/2007 | |
| JP | 2008-222859 A | 9/2008 | |
| JP | 2011-006609 A | 1/2011 | |
| JP | 2015-149929 A | 8/2015 | |
| JP | 2015-149930 A | 8/2015 | |
| JP | 2017-149901 A | 8/2017 | |
| JP | 6337225 B1 | 6/2018 | |
| JP | 6351821 B1 | 7/2018 | |
| JP | 2018-164443 A | 10/2018 | |
| JP | 6404516 B1 | 10/2018 | |
| JP | 6417490 B1 | 11/2018 | |
| JP | 6442106 B1 | 12/2018 | |
| JP | 6505900 B1 | 4/2019 | |
| JP | 6505901 B1 | 4/2019 | |
| WO | 2014/087767 A1 | 6/2014 | |
| WO | 2014/088072 A1 | 6/2014 | |
| WO | 2017/199924 A1 | 11/2017 | |
| WO | 2019/221272 A1 | 11/2019 | |

OTHER PUBLICATIONS

U.S. Appl. No. 17/056,303, filed Nov. 17, 2020.
International Search Report and Written Opinion for Application No. PCT/JP2019/019670, dated Jul. 2, 2019, 19 pages.
International Search Report and Written Opinion for Application No. PCT/JP2019/019675, dated Jun. 25, 2019, 15 pages.
Bhandari et al., Carboxymethylation of cellulose using reactive extrusion. Carbohydrate Polymers. 2012;87:2246-2254.

* cited by examiner

*Primary Examiner* — Kevin E Weddington
(74) *Attorney, Agent, or Firm* — McCarter & English, LLP

(57) ABSTRACT

This dispersion composition contains a water-based medium and a carboxymethyl cellulose having a carboxymethyl substitution degree of 0.20 or more and a cellulose-I crystallinity index of 50% or more, a water-based medium is easily dispersed even by low mixing power, and has a high viscosity.

4 Claims, No Drawings

DISPERSION COMPOSITION CONTAINING CARBOXYMETHYL CELLULOSE

CROSS-REFERENCE TO RELATED APPLICATIONS

This application is a U.S. national stage filing, under 35 U.S.C. § 371(c), of International Application No. PCT/JP2019/019675, filed on May 17, 2019, which claims priority to Japanese Patent Application No. 2018-096479, filed on May 18, 2018, and Japanese Patent Application No. 2018-182110, filed on Sep. 27, 2018.

TECHNICAL FIELD

The present invention relates to a dispersion composition containing a carboxymethyl cellulose and a water-based medium, and a method for producing the dispersion composition.

BACKGROUND ART

Carboxymethyl cellulose is a cellulose derivative, and is obtained by linking carboxymethyl groups to some of hydroxyl groups in glucose residues in cellulose backbones to thereby form ether linkages. Carboxymethyl cellulose has no toxicity and has thickening properties and thixotropic properties (thixotropy), and thus is used for, for example, thickeners or dispersion stabilizers in various fields of food/drink products, cosmetic products, pharmaceutical products, industries, architecture, and the like.

PTL 1 describes use of carboxymethyl cellulose (hereinafter, also called "CMC".) as, for example, an emulsifier or a protective colloid for emulsions, a builder for paints, adhesives, poultices, coating agents, synthetic detergents, a stabilizer for soft-serve ice creams, jams, and the like, a stabilizer for emulsion formulations, creams, and ointments, a bulk producer, or a binding agent in tablet production.

CITATION LIST

Patent Literature

PTL 1: Japanese Patent Laid-Open No. 2000-34301

SUMMARY OF INVENTION

Technical Problem

Carboxymethyl cellulose, when added to a water-based medium and used, is preferably easily dissolved or dispersed uniformly in the water-based medium. For example, carboxymethyl cellulose to be dissolved/dispersed in a water-based medium under a stirring power by a household juicer-mixer without use of any special apparatus such as a high-pressure homogenizer can be said to be very favorable in handling properties. Carboxymethyl cellulose which is sufficiently mixed with a water-based medium by such simple stirring to thereby impart high thickening properties is considered to be suitably usable as a thickener in various fields.

Carboxymethyl cellulose commonly used is generally a water-soluble polymer having no crystallinity of cellulose. On the contrary, carboxymethyl cellulose which has crystallinity of cellulose remaining therein and which partially maintains a fibrous shape without being completely dissolved in water is expected to have a new effect, for example, to be higher in shape retention ability due to its characteristics of shape and such as crystallinity.

An object of the present invention is to provide a dispersion composition containing a carboxymethyl cellulose having a particularly high degree of crystallization of cellulose type I (50% or more), and a water-based medium, in which the carboxymethyl cellulose is favorably dispersed in the water-based medium even under a stirring power by a household mixer to thereby exhibit a high viscosity.

Solution to Problem

Crystallinity of cellulose in carboxymethyl cellulose is usually lost due to a chemical treatment during its production. To keep a degree of crystallization of cellulose type I of carboxymethyl cellulose being 50% or more, it is necessary to reduce the degree of such a chemical treatment (namely, reduce the degree of carboxymethyl substitution). However, a problem is that a low degree of carboxymethyl substitution causes carboxymethyl cellulose not to be easily dispersed in a water-based medium, for example, to be precipitated under a stirring power by a household mixer.

On the contrary, the present inventors have made intensive studies, and as a result, have discovered a method for producing a carboxymethyl cellulose in which the degree of carboxymethyl substitution can be increased to 0.20 or more with a degree of crystallization of cellulose type I of 50% or more being maintained. It has been found that a carboxymethyl cellulose thus obtained, having a degree of carboxymethyl substitution of 0.20 or more, having a degree of crystallization of cellulose type I of 50% or more, and having a median diameter of about 10.0 to 150.0 μm, is uniformly dispersed in a water-based medium to thereby remarkably thicken the water-based medium, when mixed with the water-based medium under a stirring power by a household mixer (a rotational speed of 8000 to 15000 rpm).

The present invention provides the following, but is not limited thereto.

[1] A dispersion composition containing a carboxymethyl cellulose having a degree of carboxymethyl substitution of 0.20 or more and having a degree of crystallization of cellulose type I of 50% or more, and a water-based medium.

[2] The dispersion composition according to [1], wherein the carboxymethyl cellulose has a median diameter of 10.0 to 150.0 μm.

[3] The dispersion composition according to [1] or [2], having a viscosity (6 rpm, 25° C.) of 1000 m·Pas to 30000 m·Pas at a solid content of the carboxymethyl cellulose of 1% (w/v).

[4] The dispersion composition according to any one of [1] to [3], having a viscosity (60 rpm, 25° C.) of 100 m·Pas to 10000 m·Pas at a solid content of the carboxymethyl cellulose of 1% (w/v).

[5] A food or drink product containing the dispersion composition according to any one of [1] to [4].

[6] A pharmaceutical product containing the dispersion composition according to any one of [1] to [4].

[7] A cosmetic product containing the dispersion composition according to any one of [1] to [4].

[8] A feed containing the dispersion composition according to any one of [1] to [4].

[9] Paper containing the dispersion composition according to any one of [1] to [4].

[10] A paint containing the dispersion composition according to any one of [1] to [4].

[11] A method for producing a dispersion composition, including
  step 1 of preparing a mixture containing a carboxymethyl cellulose having a degree of carboxymethyl substitution of 0.20 or more and having a degree of crystallization of cellulose type I of 50% or more, and a water-based medium, and
  step 2 of subjecting the mixture obtained in step 1 to stirring at a rotational speed of 8000 to 15000 rpm for 1 minute or more, thereby obtaining a dispersion composition, wherein
  the carboxymethyl cellulose in the dispersion composition has a median diameter of 10.0 to 150.0 μm.

[12] The production method according to [11], wherein the dispersion composition has a viscosity (6 rpm, 25° C.) of 1000 mPa·s to 30000 mPa·s at a solid content of the carboxymethyl cellulose of 1% (w/v).

[13] The production method according to [11] or [12], wherein a median diameter $D_{50A}$ of the carboxymethyl cellulose before the stirring in step 2 and a median diameter $D_{50B}$ of the carboxymethyl cellulose after the stirring in step 2 satisfy the following expression:

$$90 \leq D_{50B}/D_{50A} \times 100 \leq 110.$$

Effects of Invention

The dispersion composition containing a carboxymethyl cellulose having a degree of carboxymethyl substitution of 0.20 or more and having a degree of crystallization of cellulose type I of 50% or more, and a water-based medium, of the present invention, contains carboxymethyl cellulose of which crystallinity remains, and which is favorably dispersed in the water-based medium, and has a high viscosity. Such a dispersion composition can be said to be suitable for use as, for example, a thickener or a shape retaining agent in various fields in which a water-based medium is used, for example, food products, pharmaceutical products, cosmetic products, feeds, paper, and paints.

The carboxymethyl cellulose having a degree of carboxymethyl substitution of 0.20 or more and having a degree of crystallization of cellulose type I of 50% or more is homogeneous and excellent in dispersion stability, is excellent in imparting of water retention ability and shape retention ability, is relatively less sticky even in contact with a water-based medium, and hardly forms a clump (aggregate) in water, and therefore a dispersion composition containing the carboxymethyl cellulose and a water-based medium can be suitably used for various additives such as an agent imparting water retention ability, an agent imparting shape retention ability, a viscosity modifier, an emulsion stabilizer, and a dispersion stabilizer in various fields including food products, pharmaceutical products, cosmetic products, feeds, papermaking, paints, and the like.

DESCRIPTION OF EMBODIMENTS

The present invention relates to a dispersion composition containing a specified carboxymethyl cellulose, and a water-based medium, and a method for producing the dispersion composition.

<Carboxymethyl Cellulose>

The dispersion composition of the present invention contains a carboxymethyl cellulose having a degree of carboxymethyl substitution of 0.20 or more and having a degree of crystallization of cellulose type I of 50% or more.

The carboxymethyl cellulose has a structure obtained by linking carboxymethyl groups to some of hydroxyl groups in glucose residues included in cellulose to thereby form ether linkages. The carboxymethyl cellulose may also be in the form of a salt, and the carboxymethyl cellulose for use in the present invention encompasses a carboxymethyl cellulose salt. Examples of such a carboxymethyl cellulose salt include a metal salt such as a carboxymethyl cellulose sodium salt.

<Degree of Carboxymethyl Substitution>

The carboxymethyl cellulose for use in the present invention has a degree of carboxymethyl substitution per anhydrous glucose unit of cellulose of 0.20 or more. Preferably, the degree of carboxymethyl substitution is 0.23 or more. If a degree of carboxymethyl substitution is less than 0.20, it is difficult to disperse the carboxymethyl cellulose uniformly in a water-based medium by use of an apparatus low in stirring power, like a household juicer-mixer, sedimentation occurs in a water-based medium, and desired thickening properties cannot be obtained. The upper limit value of the degree of carboxymethyl substitution is preferably 0.50 or less, more preferably 0.40 or less. If a degree of carboxymethyl substitution of more than 0.50, such carboxymethyl cellulose easily dissolves in a water-based medium, and its particle size in a water-based medium cannot be measured. Accordingly, the degree of carboxymethyl substitution is preferably in the range of 0.20 or more and 0.50 or less. In a case where a degree of carboxymethyl substitution is in the range of 0.20 or more and 0.50 or less, it was difficult to obtain a carboxymethyl cellulose having a degree of crystallization of cellulose type I of 50% or more particularly by a conventional water mediated method. The present inventors have found that a carboxymethyl cellulose which has a degree of carboxymethyl substitution of 0.20 or more and 0.50 or less and a degree of crystallization of cellulose type I of 50% or more and which is stable in quality (which provides a dispersion low in viscosity) can be produced by, for example, a production method described below. The degree of carboxymethyl substitution can be adjusted by controlling, for example, the amount of addition of a carboxymethylating agent to be reacted, the amount of a mercerizing agent, and the compositional ratio of water and an organic solvent.

The anhydrous glucose unit in the present invention means each anhydrous glucose (glucose residues) included in cellulose. The degree of carboxymethyl substitution (also referred to as "degree of etherification".) herein represents the proportion of hydroxyl groups replaced with carboxymethyl ether groups among hydroxyl groups of glucose residues included in cellulose (the number of carboxymethyl ether groups per glucose residue). The degree of carboxymethyl substitution may be here abbreviated as DS.

The method for measuring the degree of carboxymethyl substitution is as follows:

About 2.0 g of a sample is precisely weighed and is placed in a 300-mL stoppered conical flask. 100 mL of nitric acid/methanol (a liquid obtained by adding 100 mL of conc. nitric acid (special grade) to 1000 mL of methanol) is added thereto, and the resultant is shaken for 3 hours, thereby converting a salt of carboxymethyl cellulose (CMC) to H-CMC (hydrogen-type carboxymethyl cellulose). The absolute dry H-CMC is precisely weighed in an amount of 1.5 to 2.0 g and is placed in a 300-mL stoppered conical flask. The H-CMC is wetted with 15 mL of 80% methanol, 100 mL of 0.1 N—NaOH is added thereto, and the resultant is shaken at room temperature for 3 hours. Phenolphthalein is used as an indicator to reversely titrate excess NaOH by 0.1 N—$H_2SO_4$, and the degree of carboxymethyl substitution (DS value) is calculated according to the following expressions.

$$A=[(100 \times F'-0.1\text{N}—H_2SO_4(\text{mL}) \times F) \times 0.1]/(\text{Absolute dry mass(g) of H-CMC})$$

$$\text{Degree of carboxymethyl substitution}=0.162 \times A/(1-0.058 \times A)$$

F': factor of 0.1 N—$H_2SO_4$
F: factor of 0.1 N—NaOH.

<Degree of Crystallization of Cellulose Type I>

The degree of crystallization of cellulose type I in the carboxymethyl cellulose for use in the present invention is 50% or more. Preferably, the degree of crystallization is 60% or more. If a degree of crystallization of cellulose type I is less than 50%, sufficient thickening properties cannot be obtained. The crystallinity of cellulose can be controlled by the concentration of a mercerizing agent and the temperature in a treatment, as well as the degree of carboxymethylation. An alkali at a high concentration is used in mercerization and carboxymethylation to thereby allow a type I crystal of cellulose to be easily converted into a type II crystal; however, for example, the amount of the alkali (mercerizing agent) to be used can be adjusted to thereby adjust the degree of modification, thereby allowing desired crystallinity to be maintained. The upper limit of the degree of crystallization of cellulose type I is not particularly limited. The upper limit is considered to be actually about 90%.

The method for measuring the degree of crystallization of cellulose type I of the carboxymethyl cellulose is as follows:

A sample is put on a glass cell, and subjected to measurement with an X-ray diffraction diffractometer (LabX XRD-6000, manufactured by Shimadzu Corporation). The degree of crystallization is calculated according to a procedure of Segal, et al., and is calculated from the diffraction intensity of the 002 plane at $2\theta=22.6°$ and the diffraction intensity of an amorphous portion at $2\theta=18.5°$ with the diffraction intensity at $2\theta=10°$ to $30°$ as the baseline in an X-ray diffraction diagram, according to the following expressions:

$$Xc=(I002c-Ia)/I002c \times 100$$

Xc=degree of crystallization (%) of cellulose type I
I002c: diffraction intensity of 002 plane at $2\theta=22.6°$
Ia: diffraction intensity of amorphous portion at $2\theta=18.5°$.

Carboxymethyl cellulose can be commonly produced by subjecting cellulose to an alkaline treatment (mercerization) and thereafter allowing the resulting mercerized cellulose (also referred to as "alkaline cellulose".) to react with a carboxymethylating agent (also referred to as "etherifying agent".).

<Median Diameter>

The carboxymethyl cellulose for use in the present invention preferably has a median diameter of 10.0 to 150.0 μm, more preferably, 25.0 to 100.0 μm, further preferably, 35.0 to 70.0 μm. A median diameter of 10.0 μm or more is preferable because powder is hardly blown up and is easily handled, and a median diameter of 150.0 μm or less is preferable because powder has a proper size and thus is easily stuffed. It is also presumed that a median diameter in the above range allows the carboxymethyl cellulose not to be too small in fiber length and fiber diameter and to be kept in certain ranges, and thus allows the carboxymethyl cellulose to not only have favorable dispersibility, but also easily exhibit thickening properties (gelation).

The median diameter can be measured according to the following procedure:

A sample is prepared using methanol as a dispersing medium so as to have a scattering strength of 0.1 to 20%, and subjected to measurement with a laser diffraction particle size distribution measurement apparatus (Mastersizer 3000 manufactured by Malvern Panalytical Ltd.).

<Other Characteristics of Carboxymethyl Cellulose>

Carboxyl groups (—COOH) derived from carboxymethyl groups in the carboxymethyl cellulose for use in the present invention may be modified appropriately, as long as the effects of the present invention are not impaired. Examples of such modification include linking of an amine-based compound or a phosphorus-based compound having an alkyl group, an aryl group, an aralkyl group, or the like to the carboxyl group.

The carboxymethyl cellulose for use in the present invention may carry a metal, as long as the effects of the present invention are not impaired. Carrying a metal means that an aqueous solution including a metal compound is brought into contact with the carboxymethyl cellulose to allow the metal compound to link to carboxylate groups (—COO—) derived from carboxyl groups (—COOH) of carboxymethyl cellulose, by a coordination linkage or hydrogen linkage. Thus, a carboxymethyl cellulose that contains a metal compound where metal ions derived from the metal compound are ionically linked can be obtained. Examples of such a metal compound can include a metal salt including ions of one or more metal elements selected from the group consisting of Ag, Au, Pt, Pd, Mn, Fe, Ti, Al, Zn, or Cu.

The carboxymethyl cellulose for use in the present invention preferably less forms a clump (aggregate) (namely, low formation of a filtration residue), when in the form of a dispersion using a water-based medium as a dispersing medium (water dispersion). Specifically, in a case where the carboxymethyl cellulose is added to 500 g of water and the resultant is stirred at 400 rpm for 5 seconds and thereafter naturally filtered with a 20-mesh filter, the dry mass of a filtration residue on the filter is preferably 0 to 30% by mass based on the dry mass of the carboxymethyl cellulose added to water (the proportion of the dry mass of the filtration residue after the natural filtration based on the dry mass of the carboxymethylated cellulose added to water, calculated according to the above method, is herein called "the proportion of the filtration residue".). A specific method for measuring the proportion of the filtration residue is as follows:

(1) Measurement of Amount of Filtration Residue 500 g of water is collected in a 1-L beaker. Five grams of the carboxymethyl cellulose is collected and the mass thereof is recorded (mass of carboxymethyl cellulose). An impeller is installed to a stirrer (IKA® EUROSTAR P CV S1 (manufactured by IKA Corporation)), and water is stirred at 400 rpm. The carboxymethyl cellulose whose mass is recorded is added to the stirred water at once, and the resultant is stirred for 5 seconds after the addition. After completion of the stirring, the stirrer is turned off. After completion of the stirring, natural filtration is rapidly performed with a 20-mesh filter whose mass is measured in advance. After the natural filtration, the filter and a residue thereon are dried together on a tray at 100° C. for 2 hours. The mass of the filter and the residue thereon is measured, and the mass of the filter is subtracted therefrom, thereby calculating the absolute dry mass (g) of the residue (absolute dry mass of residue).

(2) Calculation of amount of moisture in carboxymethyl cellulose

A weighing bottle is heated at 100° C. for 2 hours and cooled in a desiccator with silica gel therein, and the absolute dry mass of the weighing bottle is precisely weighed (absolute dry mass of weighing bottle). About 1.5 g of the carboxymethyl cellulose is metered and taken in the weighing bottle, and precisely weighed (mass of CMC before drying). The lid of the weighing bottle is opened, and heating and drying are made at 105° C. for 2 hours. The lid of the weighing bottle is closed, and cooling is made in the desiccator with silica gel therein, for 15 minutes. The mass of the weighing bottle after drying (including the carboxymethyl cellulose after drying) is precisely weighed (mass of weighing bottle including CMC after drying). The amount of moisture in the carboxymethyl cellulose is calculated according to following expression:

Moisture (%) in carboxymethyl cellulose=[{Mass(g) of CMC before drying−(Mass(g) of weighing bottle including CMC after drying−Absolute dry mass(g) of weighing bottle)}/Mass(g) of CMC before drying]×100.

(3) Calculation of Proportion of Filtration Residue

The proportion of the filtration residue of the carboxymethyl cellulose is calculated using the mass (g) of the carboxymethylated cellulose and the absolute dry mass (g) of the residue, measured in (1), and the moisture (%) in the carboxymethyl cellulose, calculated in (2), according to the following expression:

Proportion (%) of filtration residue of carboxymethyl cellulose=[Absolute dry mass(g) of residue/{Mass(g) of carboxymethyl cellulose×(100−Moisture (%) in carboxymethyl cellulose)/100}]×100.

The proportion of the filtration residue of the carboxymethyl cellulose, calculated according to the above expression, is preferably 0 to 30%, further preferably 0 to 20%, further preferably 0 to 10%. A carboxymethyl cellulose low in proportion of the filtration residue is easily dispersed and excellent in handling properties. Such a carboxymethyl cellulose low in proportion of the filtration residue can be produced according to, for example, a method described below.

The carboxymethyl cellulose for use in the present invention preferably has a Schopper-Riegler freeness of 60.0° SR or more. The method for measuring the Schopper-Riegler freeness is according to JISP 82121-1: 2012, and is specifically as follows:

The carboxymethyl cellulose is dispersed in water to prepare a water dispersion having a solid content of 10 g/L, and the water dispersion is stirred with a magnetic stirrer at 1000 rpm all night and all day. The resulting slurry is diluted to 1 g/L. A 60-mesh screen (wire diameter: 0.17 mm) is installed to DFR-04 manufactured by Mutec Co., Ltd., the amount of a liquid passing through the mesh, in 1000 ml of a testing liquid, is measured for 60 seconds, and the Schopper-Riegler freeness is calculated by the method according to JISP 8121-1: 2012.

The Schopper-Riegler freeness is for measurement of the degree of water discharge of a fiber suspension, and the lower limit value is 0° SR, the upper limit value is 100° SR. It is indicated that, as the Schopper-Riegler freeness is closer to 100° SR, water discharge (amount of draining) is less made, namely, the water retention ability of a fiber is higher.

The carboxymethyl cellulose preferably has a Schopper-Riegler freeness of 60.0° SR or more, further preferably 65.0° SR or more. The upper limit is not particularly limited, and is 100.0° SR or less, preferably 90.0° SR or less. Carboxymethyl cellulose having a Schopper-Riegler freeness of 60.0° SR or more is high in water retention ability, and can be said to be suitable for use as, for example, a water retention agent for various compositions such as food products, cosmetic products, and pharmaceutical products, without any limitation thereto. The carboxymethyl cellulose having such a Schopper-Riegler freeness can be produced by, for example, a method described below.

The carboxymethyl cellulose for use in the present invention preferably has a Canadian standard freeness of 150 ml or less, more preferably 120 ml or less, further preferably 110 ml or less. The carboxymethyl cellulose having such a Canadian standard freeness can be produced by, for example, a method described below. The Canadian standard freeness is for measurement of the degree of water discharge of a fiber suspension, and it is indicated that, as the value is smaller, water discharge (amount of draining) is less made, namely, the water retention ability of a fiber is higher. The method for measuring the Canadian standard freeness is as follows:

A sample is prepared according to the same method as in the above Schopper-Riegler freeness, a 60-mesh screen (wire diameter: 0.17 mm) is installed to DFR-04 manufactured by Mutec Co., Ltd., the amount of a liquid passing through the mesh, in 1000 ml of a testing liquid, is measured for 60 seconds, and the Canadian standard freeness is calculated by the method according to JISP 8121-2: 2012.

The carboxymethyl cellulose for use in the present invention preferably has an amount of drainage of 400 ml or less, more preferably 380 ml or less, further preferably 370 ml or less. The carboxymethyl cellulose having such an amount of drainage can be produced by, for example, a method described below. The amount of drainage is for measurement of the degree of water discharge of a fiber suspension. It is indicated that, as the value is smaller, water discharge (amount of draining) is less made, namely, the water retention ability of a fiber is higher. The method for measuring the amount of drainage is as follows:

A sample is adjusted according to the same method as in the above Schopper-Riegler freeness, a 60-mesh screen (wire diameter: 0.17 mm) is installed to DFR-04 manufactured by Mutec Co., Ltd., the amount of a liquid passing through the mesh, in 1000 ml of a testing liquid, is measured for 60 seconds, and the amount of drainages is calculated.

The carboxymethyl cellulose for use in the present invention preferably has a degree of anionization (also referred to as "density of anionic charge".) of 0.00 meq/g or more and 1.00 meq/g or less. The method for measuring the degree of anionization is as follows:

The carboxymethyl cellulose is dispersed in water to prepare a water dispersion having a solid content of 10 g/L, and the water dispersion is stirred with a magnetic stirrer at 1000 rpm all night and all day. The resulting slurry is diluted to 0.1 g/L, thereafter 10 ml of the resultant is collected and titrated with diallyldimethylammonium chloride (DADMAC) having a normality of $1/1000$ by use of a streaming current detector (Mutek Particle Charge Detector 03), and the amount of DADMAC added until the streaming current is zero is used to calculate the degree of anionization according to the following expression:

$$q=(V\times c)/m$$

q: Degree of anionization (meq/g)
V: Amount (L) of DADMAC added until streaming current is zero
c: Concentration (meq/L) of DADMAC
m: Mass (g) of carboxymethyl cellulose in measurement sample As can be seen from the above measurement method, the "degree of anionization" corresponds to the equivalent of DADMAC required for neutralization of an anionic group per unit mass of the carboxymethyl cellulose, and also corresponds to the equivalent of anion per unit mass of the carboxymethyl cellulose.

The carboxymethyl cellulose preferably has a degree of anionization of 0.00 meq/g or more and 1.00 meq/g or less, further preferably 0.00 meq/g or more and 0.80 meq/g or less, further preferably 0.00 meq/g or more and 0.60 meq/g or less. A carboxymethyl cellulose having a degree of anionization in such a range is considered to have carboxymethyl groups not locally, but uniformly introduced into the entire cellulose, as compared with any carboxymethyl cellulose having a degree of anionization of more than 1.00 meq/g, and is considered to be able to more stably obtain a unique effect for the carboxymethyl cellulose, for example, the effect of imparting shape retention ability and water absorption ability. The carboxymethyl cellulose having such a degree of anionization can be produced by, for example, a method described below.

<Water-Based Medium>

The water-based medium in the present invention refers to a mixed solvent of water and a polar solvent that can be mixed with water at any rate. Examples of the polar solvent that can be mixed with water at any rate can include methanol, ethanol, isopropanol, isobutanol, sec-butanol, tert-butanol, methylcellosolve, ethylcellosolve, ethylene glycol, glycerin, ethylene glycol dimethyl ether, 1,4-dioxane, tetrahydrofuran, acetone, methyl ethyl ketone, N,N-dimethylformamide, N,N-dimethyl acetamide, and dimethylsulfoxide. Such polar solvents may be each singly mixed with water, or two or more kinds thereof may be mixed with water to provide a mixed solvent. In a case where water and such a polar solvent are mixed, the mixing ratio thereof is not particularly limited, and the mixing ratio may be appropriately adjusted depending on the type of a polar solvent used, and the intended use.

<Dispersion Composition>

The above carboxymethyl cellulose and water-based medium are mixed to produce a dispersion composition. The mixing ratio of the carboxymethyl cellulose and the water-based medium is not particularly limited, and, for example, the carboxymethyl cellulose may be mixed so that the ratio of the solid content of the carboxymethyl cellulose to the dispersion composition is in the range from 0.5 to 5.0% (w/v).

Any known mixing, stirring, emulsifying, or dispersing apparatus may be used in dispersion. The carboxymethyl cellulose for use in the present invention can be favorably dispersed in the water-based medium to thereby form a dispersion composition even under a stirring power by a household juicer-mixer without use of any special apparatus like a high-pressure homogenizer. Examples of such a mixer include a mixer having a rotational speed of 8000 to 15000 rpm. Such a mixer may be used for stirring for 1 minute or more, preferably about 5 to 15 minutes.

While an apparatus which can apply a strong shear force, like a high-pressure homogenizer, is used to result in a tendency to reduce the particle size of the carboxymethyl cellulose, a mixer having a rotational speed of about 8000 to 15000 rpm can be used not to cause the particle size of the carboxymethyl cellulose to be highly varied. For example, in a case where the carboxymethyl cellulose for use in the present invention is mixed with the water-based medium and the resulting mixture is subjected to stirring at a rotational speed of 8000 to 15000 rpm, the median diameter of the carboxymethyl cellulose satisfies the following expression:

$$90 \leq D_{50B}/D_{50A} \times 100 \leq 110$$

under the assumption that the median diameter of the carboxymethyl cellulose before such stirring is designated as $D_{50A}$ and the median diameter of the carboxymethyl cellulose after such stirring is designated as $D_{50B}$.

The resulting dispersion composition may be used in various applications, as it is, or may be subjected to partial drying of the water-based medium or re-dispersion in the water-based medium, and then used, if necessary. The drying method is not limited at all, and a known method can be used such as a freeze-drying method, a spray-drying method, a shelf-type drying method, a drum drying method, a belt drying method, a drying method including thinly extending on a glass plate or the like, a fluid-bed drying method, a microwave drying method, or a drying method including using a heat generating fan under reduced pressure.

<Viscosity of Dispersion Composition>

The dispersion composition of the present invention has the characteristics of exhibiting a high viscosity. In the present invention, the method for measuring the viscosity is as follows:

A dispersion composition containing carboxymethyl cellulose having a predetermined concentration is prepared. The dispersion composition is stirred at 25° C. with a stirring machine at 600 rpm for 3 hours. Thereafter, the viscosity at a predetermined rotational speed after 3 minutes is measured with a B-type viscometer (manufactured by Toki Sangyo Co., Ltd.) according to the method of JIS Z 8803.

The dispersion composition of the present invention preferably has a viscosity (25° C.) at a rotational speed of 6 rpm, of 1000 mPa·s to 30000 mPa·s, more preferably 2000 mPa·s to 25000 mPa·s, further preferably 2500 mPa·s to 20000 mPa·s at a solid content of the carboxymethyl cellulose of 1% (w/v).

The dispersion composition of the present invention preferably has a viscosity (25° C.) at a rotational speed of 60 rpm, of 100 mPa·s to 10000 mPa·s, more preferably 300 mPa·s to 5000 mPa·s, further preferably 500 mPa·s to 4000 mPa·s at a solid content of the carboxymethyl cellulose of 1% (w/v).

The viscosity of the dispersion composition varies depending on the solid content concentration of the carboxymethyl cellulose, and any dispersion composition obtained by stirring a specified carboxymethyl cellulose in the present invention under a stirring power by a juicer-mixer has the characteristics of being favorable in thickening properties as compared with any dispersion composition obtained using other carboxymethyl cellulose having the same solid content concentration.

<Application of Dispersion Composition>

The dispersion composition of the present invention exhibits a very high viscosity even in a case where the solid content of the carboxymethyl cellulose is about 1% (w/v). The carboxymethyl cellulose having a degree of carboxymethyl substitution of 0.50 or less and having a degree of crystallization of cellulose type I of 50% or more is homogeneous and excellent in dispersion stability, is excellent in imparting of water retention ability and shape retention ability, is relatively less sticky even in contact with a water-based medium, and hardly forms a clump (aggregate) in a water-based medium, and thus the dispersion composition of the present invention is considered to be applied to various applications.

The dispersion composition is considered to be used as, for example, a thickener, an agent imparting shape retention ability, an emulsion stabilizer, or a dispersion stabilizer in the field of food/drink products such as beverages (cocoa, juice, fiber/pulp-containing juice, sweet red-bean soup, amazake, probiotic drink, fruit milk, and the like), soups (corn soup, ramen soup, miso soup, consomme, and the like), sauces, dressing, ketchup, mayonnaise, jam, yogurt, whip cream, dry foods (dry processed food, instant noodle, pasta noodle, and the like), gluten-free pasta, ice cream, monaka (bean-jam-filled wafers), sherbet, polyjuice, confectionery (gummi candy, soft candy, jelly, cookie, and the like), merengue, breads (sweet bun, custard cream bread, and the like), gluten-free breads, fillings, pancakes, pastes, and edible films, without any limitation thereto. For example, the carboxymethyl cellulose for use in the present invention can be added to a commercially available beverage such as a juice, at a concentration of about 1% (w/v), and stirred and dispersed by a household mixer (a rotational speed of 8000 to 15000 rpm) for 1 minute or more, thereby remarkably thickening such a beverage. Such properties are considered to be applied for a food product which allows a household dessert (for example, jelly) to be made.

The dispersion composition is considered to be used also as, for example, a thickener, an agent imparting shape retention ability, an emulsion stabilizer, or a dispersion stabilizer in the field of pharmaceutical products such as tablets, ointments, adhesive tapes, poultices, hand creams, and toothpastes, without any limitation thereto.

The dispersion composition is considered to be used as, for example, a thickener, an agent imparting shape retention ability, an emulsion stabilizer, or a dispersion stabilizer in the field of cosmetic products such as face powders, foundations, scrub agents for face washing, packs, cleansing foams, cleansing creams, hair mousses, shampoos, soap, lotions, hair colors, hair bleaches, mascara, eyeliners, manicures, and antiperspirants, without any limitation thereto.

The dispersion composition is considered to be used as, for example, a thickener, an agent imparting shape retention ability, an emulsion stabilizer, or a dispersion stabilizer in the field of feeds such as moist pellets and expansion pellets for domestic animals or cultured fishes, and milk substitutes for cattle, without any limitation thereto.

The dispersion composition is considered to be used as, for example, a thickener, an agent imparting shape retention ability, an emulsion stabilizer, or a dispersion stabilizer in the field of papermaking, for example, in surface sizing agents, yield improving agents, paper strengthening agents, coating agents, and agents for bulky paper, without any limitation thereto.

The dispersion composition is considered to be used as, for example, a thickener, an emulsion stabilizer, or a dispersion stabilizer in the field of paints such as matte paints, paints for building, and automobile interior paints, without any limitation thereto.

The dispersion composition of the present invention additionally exhibits a high viscosity, and thus the dispersion composition of the present invention can be used in various fields in which thickening properties are desired. The dispersion composition can be used in not only the above food/drink products, pharmaceutical product, cosmetic products, feeds, papermaking, and paints, but also, for example, various chemical goods, spray, agricultural chemicals, civil engineering, architecture, electronic materials, flame retardants, household products, adhesives, detergents, aromatic substances, lubricant compositions, polishing agents, compounding materials for rubber or plastics, mud adjusters, filtration aids, and mud overflow inhibitors, without any limitation thereto, and can also be used as, for example, a building material such as a fiber wall, a sand wall, or a gypsum board; civil engineering such as foam shielding or a water sealant for a continuous wall; a resin filler or a compound such as foamed polystyrene, a biodegradable resin, rubber, ceramic, or vinyl chloride; a dispersant for dispersing fine particles such as particles of carbon black, barium sulfate (X-ray contrast agent), titanium oxide, or zing oxide; a moisture absorbent aid for a deliquescent agent such as calcium chloride and for an improvement in shape retention ability during moisture absorption by the agent; a modifier for fibers (cloth, yarn); a liquid carrier; a lubricating oil; ceramic engineering; cat sand; a water absorption material for a desiccant; a greening construction method; or a binder.

<Method for Producing Dispersion Composition>

The dispersion composition of the present invention can be produced by a method including step 1 of preparing a mixture including a carboxymethyl cellulose having a degree of carboxymethyl substitution of 0.20 or more and having a degree of crystallization of cellulose type I of 50% or more, and a water-based medium, and step 2 of subjecting the mixture obtained in step 1 to stirring at a rotational speed of 8000 to 15000 rpm for 1 minute or more, thereby obtaining a dispersion composition. The carboxymethyl cellulose in the resulting dispersion composition has a median diameter of 10.0 to 150.0 μm. The dispersion composition preferably has a viscosity (6 rpm, 25° C.) of 1000 mPa·s to 30000 mPa·s at a solid content of the carboxymethyl cellulose of 1% (w/v).

<Step 1>

In step 1, a mixture is prepared, which includes a carboxymethyl cellulose having a degree of carboxymethyl substitution of 0.20 or more and having a degree of crystallization of cellulose type I of 50% or more, and a water-based medium. The carboxymethyl cellulose having a degree of carboxymethyl substitution of 0.20 or more and having a degree of crystallization of cellulose type I of 50% or more can be produced by, for example, the following production method, without any limitation thereto.

<Method for Producing Carboxymethyl Cellulose>

Carboxymethyl cellulose can be commonly produced by subjecting cellulose to an alkaline treatment (mercerization) and thereafter allowing the resulting mercerized cellulose (also referred to as "alkaline cellulose".) to react with a carboxymethylating agent (also referred to as "etherifying agent".). Commonly known methods for producing carboxymethyl cellulose include a water mediated method which is a method including performing both mercerization and carboxymethylation in water as a solvent, and a solvent mediated method which is a method including performing both mercerization and carboxymethylation in a solvent containing mainly an organic solvent. The carboxymethyl cellulose having a specified degree of carboxymethyl substitution and a specified degree of crystallization of cellulose type I, for use in the present invention, can be produced by, for example, mercerization (alkaline treatment of cellulose) in a solvent containing mainly water and thereafter carboxymethylation (also referred to as "etherification".) in a mixed solvent of water and an organic solvent, without any limitation thereto. Such a carboxymethyl cellulose thus obtained has the characteristics of not only having a degree of carboxymethyl substitution of 0.20 or more, but also keeping a high degree of crystallization of cellulose type I, which have been hardly achieved by any carboxymethyl cellulose obtained by according to a conventional water mediated method or solvent mediated method.

<Cellulose>

The cellulose herein means polysaccharide having a structure in which D-glucopyranoses (also simply referred to as "glucose residue" or "anhydrous glucose".) are connected by β-1,4 linkages. Celluloses are commonly classified to, for example, native cellulose, regenerated cellulose, fine cellulose, and microcrystalline cellulose from which an amorphous region is removed, depending on the source, the production method, and like. Any of such celluloses can be used as a raw material of the mercerized cellulose in the present invention, and cellulose high in degree of crystallization of cellulose type I is preferably used as a raw material in order that a degree of crystallization of cellulose type I of 50% or more is maintained in the carboxymethyl cellulose. The degree of crystallization of cellulose type I of the cellulose as a raw material is preferably, 70% or more, further preferably 80% or more. The method for measuring the degree of crystallization of cellulose type I is as described above.

Examples of the native cellulose include bleached pulp and unbleached pulp (bleached wood pulp or unbleached wood pulp); linter and refined linter; and cellulose produced by microorganisms such as acetic acid bacteria. The raw material of the bleached pulp or unbleached pulp is not particularly limited, and examples thereof include wood, cotton, straw, bamboo, hemp, jute, and kenaf. The method for producing the bleached pulp or unbleached pulp is also not particularly limited, and may be a mechanical method, a chemical method, or a combined intermediate method between these two methods. Examples of the bleached pulp or unbleached pulp classified according to the production method include mechanical pulp (thermomechanical pulp (TMP), groundwood pulp) and chemical pulp (sulfite pulp such as softwood unbleached sulfite pulp (NUSP) and softwood bleached sulfite pulp (NBSP), and kraft pulp such as softwood unbleached kraft pulp (NUKP), softwood bleached kraft pulp (NBKP), hardwood unbleached kraft pulp (LUKP), and hardwood bleached kraft pulp (LBKP)). Dissolving pulp may also be used, besides papermaking pulp. Dissolving pulp is pulp chemically refined, and is mainly used in a dissolved state in chemicals and serves as a main raw material of an artificial fiber, cellophane, or the like.

Examples of the regenerated cellulose include one obtained by dissolving cellulose in a solvent such as a cuprammonium solution, a cellulose xanthate solution, or a morpholine derivative, and subjecting the resultant to spinning. Examples of the fine cellulose include one obtained by subjecting a cellulose-based material, for example, the native cellulose or regenerated cellulose, to a depolymerization treatment (for example, acid hydrolysis, alkali hydrolysis, enzymatic degradation, a blasting treatment, or a vibration ball mill treatment), and one obtained by mechanically treating the cellulose-based material.

<Mercerization>

The above cellulose is used as a raw material and a mercerizing agent (alkali) is added, thereby obtaining mercerized cellulose (also referred to as "alkaline cellulose".). Carboxymethyl cellulose satisfying both a specified degree of carboxymethyl substitution and a specified degree of crystallization of cellulose type I can be obtained in an economic manner by a method in which water is mainly used as the solvent in the mercerization reaction and a mixed solvent of an organic solvent and water is used as the solvent in the next carboxymethylation.

"Water is mainly used in the solvent (solvent containing mainly water)" refers to a solvent containing water at a proportion of more than 50% by mass. The solvent containing mainly water preferably contains 55% by mass or more, more preferably 60% by mass or more, more preferably 70% by mass or more, more preferably 80% by mass or more, further preferably 90% by mass or more, further preferably 95% by mass or more of water. A particularly preferable solvent containing mainly water is a solvent containing 100% by mass of water (namely, water). A higher proportion of water in mercerization provides the advantage of more uniform introduction of carboxymethyl groups into cellulose. Examples of the solvent (which is mixed with water) other than water in the solvent containing mainly water include an organic solvent for use as a solvent in carboxymethylation at a later stage. Examples can include alcohols such as methanol, ethanol, n-propyl alcohol, isopropyl alcohol, n-butanol, isobutanol, and tert-butanol, ketones such as acetone, diethyl ketone, and methyl ethyl ketone, and dioxane, diethyl ether, benzene and dichloromethane, and these can be added singly or as a mixture of two or more thereof in an amount of less than 50% by mass, to water, and the resultant can be used as the solvent in mercerization. The solvent containing mainly water preferably contains 45% by mass or less, further preferably 40% by mass or less, further preferably 30% by mass or less, further preferably 20% by mass or less, further preferably 10% by mass or less, further preferably 5% by mass or less, more preferably 0% by mass of an organic solvent.

Examples of the mercerizing agent include alkali metal hydroxides such as lithium hydroxide, sodium hydroxide, and potassium hydroxide, and these can be used singly or in combinations of any two or more thereof. The mercerizing agent is not limited thereto, and such an alkali metal hydroxide can be added to a reactor, for example, in the form of an aqueous solution thereof, having, for example, a concentration of 1 to 60% by mass, preferably 2 to 45% by mass, more preferably 3 to 25% by mass.

The amount of the mercerizing agent used may be any amount and is not particularly limited as long as the carboxymethyl cellulose can satisfy both a degree of carboxymethyl substitution of 0.20 or more and a degree of crystallization of cellulose type I of 50% or more, and, in one embodiment, the amount is preferably 0.1 mol or more and 2.5 mol or less, more preferably 0.3 mol or more and 2.0 mol or less, further preferably 0.4 mol or more and 1.5 mol or less based on 100 g (absolute dry) of cellulose.

The amount of the solvent containing mainly water in mercerization is preferably an amount which can allow for stirring and mixing of a raw material, and is not particularly limited thereto. The amount is preferably 1.5 to 20 times by mass, more preferably 2 to 10 times by mass, relative to a cellulose raw material.

A mercerization treatment is performed by mixing a starting raw material (cellulose) and the solvent containing mainly water, adjusting the temperature of a reactor to 0 to 70° C., preferably 10 to 60° C., more preferably 10 to 40° C., adding an aqueous mercerizing agent solution, and stirring the resultant for 15 minutes to 8 hours, preferably 30 minutes to 7 hours, more preferably 30 minutes to 3 hours. Thus, the mercerized cellulose (alkaline cellulose) is obtained.

The pH in mercerization is preferably 9 or more, and thus the mercerization reaction can progress. The pH is more preferably 11 or more, further preferably 12 or more, and may be 13 or more. The upper limit of the pH is not particularly limited.

Such mercerization can be performed by use of a reaction machine in which the respective components can be mixed and stirred with the temperature being controlled, and any of various reaction machines conventionally used in a mercerization reaction can be used. For example, a batch type stirring apparatus in which the respective components are mixed under stirring with two screws is preferable from both viewpoints of uniform mixing ability and productivity.

<Carboxymethylation>

A carboxymethylating agent (also referred to as "etherifying agent".) is added to the mercerized cellulose, thereby obtaining carboxymethyl cellulose. Carboxymethyl cellulose satisfying both a specified degree of carboxymethyl substitution and a specified degree of crystallization of cellulose type I can be obtained in an economic manner by a method in which water is mainly used as the solvent in the mercerization reaction and a mixed solvent of an organic solvent and water is used as the solvent in the next carboxymethylation.

Examples of the carboxymethylating agent include monochloroacetic acid, sodium monochloroacetate, methyl monochloroacetate, ethyl monochloroacetate, and isopropyl monochloroacetate. In particular, monochloroacetic acid or sodium monochloroacetate is preferable in terms of their availability.

The amount of the carboxymethylating agent used may be any amount and is not particularly limited as long as the carboxymethyl cellulose can satisfy both a degree of carboxymethyl substitution of 0.20 or more and a degree of crystallization of cellulose type I of 50% or more, and, in one embodiment, the carboxymethylating agent is preferably added in the range from 0.5 to 1.5 mol per anhydrous glucose unit of cellulose. The above range more preferably has a lower limit of 0.6 mol or more, further preferably 0.7 mol or more, and more preferably has an upper limit of 1.3 mol or less, further preferably 1.1 mol or less. The carboxymethylating agent, but is not limited to, can be added to a reactor, in the form of an aqueous solution having, for example, a concentration of 5 to 80% by mass, more preferably 30 to 60% by mass, or can be added in the form of a powder with being not dissolved.

The molar ratio of the mercerizing agent to the carboxymethylating agent (mercerizing agent/carboxymethylating agent), generally adopted, is 0.90 to 2.45 in a case where monochloroacetic acid or sodium monochloroacetate is used as the carboxymethylating agent. The reason for this is because a molar ratio of less than 0.90 can cause a carboxymethylation reaction to be insufficient, resulting in remaining of the unreacted monochloroacetic acid or sodium monochloroacetate and thus diseconomy, and a molar ratio of more than 2.45 can cause a side reaction of an excess of the mercerizing agent with monochloroacetic acid or sodium monochloroacetate to progress, probably resulting in production of a glycolic acid alkali metal salt and thus the risk of diseconomy.

The rate of effective utilization of the carboxymethylating agent in carboxymethylation is preferably 15% or more, more preferably 20% or more, further preferably 25% or more, particularly preferably 30% or more. The rate of effective utilization of the carboxymethylating agent refers to the proportion of carboxymethyl groups introduced into cellulose in carboxymethyl groups in the carboxymethylating agent. The solvent containing mainly water can be used in mercerization and the mixed solvent of water and an organic solvent can be used in carboxymethylation, thereby producing the carboxymethyl cellulose for use in the present invention at a high rate of effective utilization of the carboxymethylating agent (namely, in an economic manner without use of large amount of the carboxymethylating agent). The upper limit of the rate of effective utilization of the carboxymethylating agent is not particularly limited, and the lower limit is actually about 80%. The rate of effective utilization of the carboxymethylating agent may be here abbreviated as AM.

The method for calculating the rate of effective utilization of the carboxymethylating agent is as follows:

$AM=(DS \times \text{Number of moles of cellulose})/\text{Number of moles of carboxymethylating agent}$ $DS$:Degree of carboxymethyl substitution(the measurement method will be described below)

Number of moles of cellulose: Mass of pulp (Dry mass after drying at 100° C. for 60 minutes)/162

(162 means the molecular weight per glucose unit of cellulose).

The concentration of the raw material of cellulose in the carboxymethylation reaction is not particularly limited, and is preferably 1 to 40% (w/v) from the viewpoint of an increase in rate of effective utilization of the carboxymethylating agent.

The carboxymethylation reaction is allowed to progress in a mixed solvent of water and an organic solvent, the mixed solvent of water and an organic solvent being formed by appropriately adding an organic solvent or an aqueous solution of an organic solvent to a reactor or appropriately decreasing the organic solvent or the like other than water in the mercerization treatment, for example, under reduced pressure, at the same time as addition of the carboxymethylating agent or before or immediately after addition of the carboxymethylating agent. The timing of addition or decrease of the organic solvent may be any timing and is not particularly limited as long as it is within the time from completion of the mercerization reaction to the time immediately after addition of the carboxymethylating agent, and is preferably, for example, within 30 minutes before or after addition of the carboxymethylating agent.

Examples of the organic solvent can include alcohols such as methanol, ethanol, n-propyl alcohol, isopropyl alcohol, n-butanol, isobutanol, and tert-butanol, ketones such as acetone, diethyl ketone, and methyl ethyl ketone, and dioxane, diethyl ether, benzene and dichloromethane, and these can be added singly or as a mixture of two or more thereof, to water, and the resultant can be used as the solvent in carboxymethylation. In particular, a monohydric alcohol having 1 to 4 carbon atoms is preferable and a monohydric alcohol having 1 to 3 carbon atoms is further preferable, because of being excellent in compatibility with water.

The proportion of the organic solvent in the mixed solvent in carboxymethylation is preferably 20% by mass or more, more preferably 30% by mass or more, further preferably 40% by mass or more, further preferably 45% by mass or more, particularly preferably 50% by mass or more, based on the total of water and the organic solvent. As the proportion of the organic solvent is higher, uniform substitution of carboxymethyl groups more easily occurs, and, for example, an advantage is that carboxymethyl cellulose which is stable in quality is obtained. The upper limit of the proportion of the organic solvent is not limited, and may be, for example, 99% by mass or less. The upper limit is preferably 90% by mass or less, further preferably 85% by mass or less, further preferably 80% by mass or less, further preferably 70% by mass or less in consideration of the cost of the organic solvent added.

The reaction medium (the mixed solvent of water and the organic solvent, containing no cellulose) in carboxymethylation is preferably lower in proportion of water than the reaction medium in mercerization (in other words, higher in proportion of the organic solvent). Such a range can be satisfied to thereby allow the degree of crystallization of the resulting carboxymethyl cellulose to be easily maintained and allow the carboxymethyl cellulose for use in the present invention to be more efficiently obtained. In a case where the reaction medium in carboxymethylation is lower in proportion of water than the reaction medium in mercerization (higher in proportion of the organic solvent), an advantage is that the mixed solvent for the carboxymethylation reaction can be obtained by a simple procedure in which a desired amount of the organic solvent is added to the reaction system after completion of the mercerization reaction, in transferring from the mercerization reaction to the carboxymethylation reaction.

After the mixed solvent of water and an organic solvent is formed and the carboxymethylating agent is added to the mercerized cellulose, the resultant is stirred for 15 minutes to 4 hours, preferably about 15 minutes to 1 hour with the temperature being preferably kept constantly in the range from 10 to 40° C. A liquid containing the mercerized cellulose is preferably mixed with the carboxymethylating agent in portions or by dropping in order to prevent the reaction mixture from being at a high temperature. After the carboxymethylating agent is added and stirred for a certain time, the temperature is, if necessary, raised so that the reaction temperature is 30 to 90° C., preferably 40 to 90° C., further preferably 60 to 80° C. An etherification (carboxymethylation) reaction is performed for 30 minutes to 10 hours, preferably 1 hour to 4 hours, thereby obtaining carboxymethyl cellulose. An advantage is that such a temperature rise in the carboxymethylation reaction allows the etherification reaction to be efficiently performed in a short time.

The reactor used in carboxymethylation may be the reactor used in mercerization or another reactor in which the respective components can be mixed and stirred with the temperature being controlled.

After completion of the reaction, the remaining alkali metal salt may be neutralized with a mineral acid or organic acid. If necessary, an inorganic salt, an organic acid salt, and/or the like as by-product(s) may be removed by washing with water-containing methanol, and the resultant may be dried, pulverized and classified to form the carboxymethyl cellulose or the salt thereof. Examples of the apparatus for use in dry pulverization include impact mills such as a hammer mill and a pin mill, medium mills such as a ball mill and a tower mill, and jet mills. Examples of the apparatus for use in wet pulverization include apparatuses such as a homogenizer, a masscolloider, and a pearl mill.

<Mixture Including Carboxymethyl Cellulose and Water-Based Medium>

Subsequently, a mixture is obtained by mixing a carboxymethyl cellulose having a specified degree of carboxymethyl substitution and a specified degree of crystallization of cellulose type I, with a water-based medium. The water-based medium is as described above. The mixing ratio of the water-based medium and the carboxymethyl cellulose is not particularly limited, and the ratio of the solid content of the carboxymethyl cellulose to the mixture is preferably 0.5 to 5.0% (w/v), further preferably 0.8 to 3.0% (w/v) in order to allow a stirring treatment to efficiently progress in the next step 2.

<Step 2>

In step 2, a dispersion composition is obtained by subjecting the mixture obtained in step 1 to stirring at a rotational speed of 8000 to 15000 rpm for 1 minute or more.

Such stirring may be made by using any apparatus which can achieve a rotational speed of 8000 to 15000 rpm. Examples of such an apparatus include, but not limited to, a juicer-mixer and a homomixer.

The stirring is performed at a rotational speed of 8000 to 15000 rpm for 1 minute or more, preferably, about 5 to 15 minutes.

The median diameter $D_{50A}$ of the carboxymethyl cellulose before the stirring in step 2 and the median diameter $D_{50B}$ of the carboxymethyl cellulose after the stirring in step 2 preferably satisfy the following expression:

$$90 \leq D_{50B}/D_{50A} \times 100 \leq 110.$$

In other words, the stirring preferably allows the median diameter of the carboxymethyl cellulose not to be significantly changed. The method for measuring the median diameter is as described above. In the present invention, a carboxymethyl cellulose-containing dispersion composition exhibiting a high viscosity can be thus produced even by use of an apparatus low in stirring power, the apparatus having almost no effect on the median diameter of the carboxymethyl cellulose.

EXAMPLES

Hereinafter, the present invention will be more specifically described with reference to Examples and Comparative Examples, but the present invention is not limited thereto. Unless especially noted, "part(s)" and "%" represent "part(s) by mass" and "% by mass", respectively.

(Production Example 1)

To a twin-screw kneader whose rotational speed was modulated to 100 rpm, was added a solution of 20 parts of sodium hydroxide in 100 parts of water, and hardwood pulp (manufactured by Nippon Paper Industries Co., Ltd., LBKP) was added thereto in an amount of 100 parts in terms of dry mass in drying at 100° C. for 60 minutes. The resultant was stirred and mixed at 30° C. for 90 minutes, thereby preparing mercerized cellulose. After 230 parts of isopropanol (IPA) and 60 parts of sodium monochloroacetate were added with further stirring and the resultant was stirred for 30 minutes, the temperature was raised to 70° C., thereby allowing for a carboxymethylation reaction for 90 minutes. The concentration of IPA in the reaction medium in the carboxymethylation reaction was 70%. After completion of the reaction, the resultant was neutralized with acetic acid to a pH of about 7, and subjected to removal of liquid, drying, and pulverization, thereby obtaining a carboxymethyl cellulose sodium salt, having a degree of carboxymethyl substitution of 0.24, a degree of crystallization of cellulose type I of 71%, and a median diameter of 59.0 µm ($D_{50A}$). The methods for measuring the degree of carboxymethyl substitution, the degree of crystallization of cellulose type I, and the median diameter are as described above.

The resulting carboxymethyl cellulose sodium salt was added to water, and the solid content of the carboxymethyl cellulose was adjusted to 1% (w/v). The resulting mixture of the carboxymethyl cellulose and water was subjected to stirring with a household juicer-mixer (product name: mixer YM-B12D1, manufacturer: HERB Relax) at a rotational speed of 10500 rpm for 10 minutes. The viscosity (25° C., rotational speed: 6 rpm or 60 rpm) of the resulting dispersion composition was measured according to the above method. The median diameter ($D_{50B}$) of the carboxymethyl cellulose was measured. The results are shown in Table 1.

(Production Example 2)

A carboxymethyl cellulose sodium salt was obtained in the same manner as in Production Example 1 except that the amount of IPA added was changed from 230 parts to 280 parts. The degree of carboxymethyl substitution was 0.31, the degree of crystallization of cellulose type I was 69%, and the median diameter was 58.1 µm ($D_{50A}$).

The resulting carboxymethyl cellulose sodium salt was added to water, the solid content of the carboxymethyl cellulose was adjusted to 1% (w/v), and the resultant was treated by a household juicer-mixer in the same manner as in Production Example 1. The results of measurement of the median diameter ($D_{50B}$) of the carboxymethyl cellulose after the treatment are shown in Table 1.

(Production Example 3)

A carboxymethyl cellulose sodium salt was obtained in the same manner as in Production Example 1 except that the amount of IPA added was changed from 230 parts to 400 parts. The degree of carboxymethyl substitution was 0.45, the degree of crystallization of cellulose type I was 65%, and the median diameter was 54.4 µm ($D_{50A}$).

The resulting carboxymethyl cellulose sodium salt was added to water, the solid content of the carboxymethyl cellulose was adjusted to 1% (w/v), and the resultant was treated by a household juicer-mixer in the same manner as in Production Example 1. The results of measurement of the median diameter ($D_{50B}$) of the carboxymethyl cellulose after the treatment are shown in Table 1.

(Comparative Production Example 1)

A carboxymethylated cellulose sodium salt was obtained in the same manner as in Production Example 1 except that the solvent in the mercerization reaction contained 10% of water and 90% of IPA, and 15 parts of sodium hydroxide was used in mercerization and 45 parts of sodium monochloroacetate was used in the carboxymethylation reaction. The degree of carboxymethyl substitution was 0.15, the degree of crystallization of cellulose type I was 69%, and the median diameter was 56.3 µm ($D_{50A}$).

The resulting carboxymethyl cellulose sodium salt was added to water, the solid content of the carboxymethyl cellulose was adjusted to 1% (w/v), and the resultant was treated by a household juicer-mixer in the same manner as in Production Example 1. The results of measurement of the median diameter (D50B) of the carboxymethyl cellulose after the treatment are shown in Table 1.

(Comparative Production Example 2)

A carboxymethylated cellulose sodium salt was obtained in the same manner as in Example 1 except that the solvent in the mercerization reaction contained 30% of water and 70% of IPA, and 68 parts of sodium hydroxide was used in mercerization and 80 parts of not sodium monochloroacetate, but monochloroacetic acid was added in the carboxymethylation reaction. The degree of carboxymethyl substitution was 0.29, the degree of crystallization of cellulose type I was 0%, and the median diameter was 51.4 µm ($D_{50A}$).

The resulting carboxymethyl cellulose sodium salt was added to water, the solid content of the carboxymethyl cellulose was adjusted to 1% (w/v), and the resultant was treated by a household juicer-mixer in the same manner as in Example 1. The resulting dispersion composition was subjected to the same measurements of the viscosity and the median diameter ($D_{50B}$) as in Example 1. The results are shown in Table 1.

<Method for Evaluating Dripping>

Ten grams of each of the dispersion compositions (solid content: 1% (w/v)) obtained in Production Examples 1 to 3 and Comparative Production Examples 1 and 2, treated by a juicer-mixer, was placed near the center of a plastic plate of 30 cm×30 cm with a dropper, and left to stand still. Thereafter, the plastic plate was inclined at an angle of 30 degrees, and the state of such each dispersion composition was visually confirmed.

Good: the dispersion composition stood firm and no dripping occurred.

Poor: the dispersion composition started to flow and dripping occurred.

TABLE 1

| | Carboxy-methyl cellulose | Solvent in mercerization | | Solvent in carboxy-methylation | | Degree of carboxy-methyl substitution | Degree of crystallization of cellulose type I | Median diameter $D_{50B}$ (µm) | Viscosity at 1% (mPa · s) | | $D_{50B}/D_{50A}$ | Less dripping |
|---|---|---|---|---|---|---|---|---|---|---|---|---|
| | | Water | IPA | Water | IPA | | | | 6 rpm | 60 rpm | | |
| Example 1 | Production Example 1 | 100% | 0% | 30% | 70% | 0.24 | 71% | 59.2 | 3820 | 920 | 1.00 | Good |
| Example 2 | Production Example 2 | 100% | 0% | 30% | 70% | 0.31 | 69% | 58.1 | 8200 | 1200 | 1.00 | Good |
| Example 3 | Production Example 3 | 100% | 0% | 30% | 70% | 0.45 | 65% | 54.4 | 19000 | 1500 | 1.00 | Good |
| Comparative Example 1 | Comparative Production Example 1 | 10% | 90% | 10% | 90% | 0.15 | 69% | 56.3 | Unmeasurable due to occurrence of precipitate | | 1.00 | — |
| Comparative Example 2 | Comparative Production Example 2 | 30% | 70% | 30% | 70% | 0.29 | 0% | 51.4 | 2440 | 510 | 1.00 | Poor |

It has been found from the results in Table 1 that the dispersion composition of the present invention (Examples 1 to 3) containing a carboxymethyl cellulose having a degree of carboxymethyl substitution of 0.20 or more, a degree of crystallization of cellulose type I of 50% or more, and a median diameter ($D_{50B}$) of 10.0 to 150.0 µm, and water exhibits a high viscosity at a solid content of the carboxymethyl cellulose of 1% (w/v). Comparative Example 1 in which, while the degree of crystallization of cellulose type I was 50% or more, the degree of carboxymethyl substitution was less than 0.20, caused no dispersion in water by stirring with a juicer-mixer, caused a precipitate and the viscosity could not be measured. Comparative Example 2 in which the amount of chemicals was increased to enhance the degree of carboxymethyl substitution in a conventional solvent mediated method was found to have no crystallinity and also to have a slightly low viscosity at 1%. While each of the dispersion compositions of Examples 1 to 3 was solidified in the form of gel (to such an extent that no flowing occurred even if inclined) in evaluation of dripping, the dispersion composition of Comparative Example 2 flowed if inclined. Comparative Example 1 caused the carboxymethyl cellulose to be precipitated to thereby provide no dispersion composition, and thus was not subjected to evaluation of dripping.

<Evaluation of Thickening Properties in Food Product>

Each of the carboxymethyl cellulose sodium salts obtained in Production Examples 1 to 3 and Comparative Production Examples 1 and 2 was added to water, and the solid content of the carboxymethyl cellulose was adjusted to 1% (w/v). A cocoa powder (Van Houten® pure cocoa) was added thereto so that the solid content was 1% (w/v), and the resulting mixture was subjected to stirring with a household juicer-mixer (product name: mixer YM-B12D1, manufacturer: HERB Relax) at a rotational speed of 10500 rpm for 10 minutes. The viscosity (25° C., rotational speed: 6 rpm or 60 rpm) of the resulting dispersion composition was measured according to the above method. The dispersibility of the dispersion composition was visually confirmed. The results are shown in Table 2.

Good: cocoa was maintained in the state of being dispersed even after still standing for 3 hours.

Poor: cocoa was sedimented after still standing for 3 hours.

TABLE 2

| | Carboxy-methyl cellulose | Viscosity in cocoa (mPa · s) | | Dispersibility |
| --- | --- | --- | --- | --- |
| | | 6 rpm | 60 rpm | |
| Example 4 | Production Example 1 | 1200 | 147 | Good |
| Example 5 | Production Example 2 | 2150 | 288 | Good |
| Example 6 | Production Example 3 | 9441 | 1300 | Good |
| Comparative Example 3 | Comparative Production Example 1 | — | — | — |
| Comparative Example 4 | Comparative Production Example 2 | 500 | 90 | Poor |

It has been found from the results in Table 2 that the dispersion composition of the present invention (Examples 4 to 6) is high in thickening properties and also high in dispersibility even if is in a food product containing a cocoa powder. Comparative Example 3 caused the carboxymethyl cellulose to be precipitated to thereby provide no dispersion composition, and thus was not subjected to viscosity measurement and dispersibility evaluation.

<Evaluation of Thickening Properties in Paint>

Each of the carboxymethyl cellulose sodium salts obtained in Production Examples 1 to 3 and Comparative Production Examples 1 and 2 was added in an amount of 1% by mass, to an aqueous paint of an aminoalkyd-based resin (solid content: 55%). The resulting mixture was subjected to stirring with a household juicer-mixer (product name: mixer YM-B12D1, manufacturer: HERB Relax) at a rotational speed of 10500 rpm for 10 minutes. The viscosity (25° C., rotational speed: 6 rpm or 60 rpm) of the resulting dispersion composition was measured according to the above method. The dispersibility of the dispersion composition was visually confirmed. The results are shown in Table 3.

Good: the dispersion state was maintained even after still standing for 1 day.

Fair: the dispersion state was maintained after still standing for 5 hours, but any precipitate was partially observed after still standing for 1 day.

Poor: any precipitate was observed after still standing for 5 hours.

TABLE 3

| | Carboxymethyl cellulose | Dispersibility |
| --- | --- | --- |
| Example 7 | Production Example 1 | Good |
| Example 8 | Production Example 2 | Good |
| Example 9 | Production Example 3 | Good |
| Comparative Example 5 | Comparative Production Example 1 | — |
| Comparative Example 6 | Comparative Production Example 2 | Fair |

It has been found from the results in Table 3 that the dispersion composition of the present invention (Examples 7 to 9) is high in dispersibility in a paint. Comparative Example 5 caused the carboxymethyl cellulose to be precipitated to thereby provide no dispersion composition, and thus was not subjected to dispersibility evaluation.

<Evaluation of Thickening Properties in Cosmetic Product>

Each of the carboxymethyl cellulose sodium salts obtained in Production Examples 1 to 3 and Comparative Production Examples 1 and 2 was added to water, and the solid content of the carboxymethyl cellulose was adjusted to 1% (w/v). Glycerin (manufactured by FUJIFILM Wako Pure Chemical Corporation) was added thereto so that its content was 10% (v/v). The resulting mixture was subjected to stirring with a household juicer-mixer (product name: mixer YM-B12D1, manufacturer: HERB Relax) at a rotational speed of 10500 rpm for 10 minutes. The viscosity (25° C., rotational speed: 6 rpm or 60 rpm) of the resulting dispersion composition was measured according to the above method. The dispersibility of the dispersion composition was visually confirmed. The results are shown in Table 4.

Good: the dispersion state was maintained even after still standing for 1 day.

Poor: separation was observed after still standing for 1 day.

TABLE 4

| | Carboxy-methyl cellulose | Viscosity in lotion (mPa · s) | | Dispersibility |
| --- | --- | --- | --- | --- |
| | | 6 rpm | 60 rpm | |
| Example 10 | Production Example 1 | 3510 | 820 | Good |
| Example 11 | Production Example 2 | 7400 | 1050 | Good |
| Example 12 | Production Example 3 | 17000 | 1320 | Good |
| Comparative Example 7 | Comparative Production Example 1 | — | — | — |

TABLE 4-continued

| | Carboxy-methyl cellulose | Viscosity in lotion (mPa · s) | | Dispersibility |
|---|---|---|---|---|
| | | 6 rpm | 60 rpm | |
| Comparative Example 8 | Comparative Production Example 2 | 1800 | 390 | Poor |

It has been found from the results in Table 4 that the dispersion composition of the present invention (Examples 10 to 12) is high in thickening properties and also high in dispersibility even in a lotion containing glycerin. Comparative Example 7 caused the carboxymethyl cellulose to be precipitated to thereby provide no dispersion composition, and thus was not subjected to viscosity measurement and dispersibility evaluation.

(Production Example 4)

To a twin-screw kneader whose rotational speed was modulated to 100 rpm, were added 130 parts of water and a solution of 20 parts of sodium hydroxide in 100 parts of water, and hardwood pulp (manufactured by Nippon Paper Industries Co., Ltd., LBKP) was added thereto in an amount of 100 parts in terms of dry mass in drying at 100° C. for 60 minutes. The resultant was stirred and mixed at 30° C. for 90 minutes, thereby preparing mercerized cellulose. After 100 parts of isopropanol (IPA) and 60 parts of sodium monochloroacetate were added with further stirring and the resultant was stirred for 30 minutes, the temperature was raised to 70° C., thereby allowing for a carboxymethylation reaction for 90 minutes. The concentration of IPA in the reaction medium in the carboxymethylation reaction was 30%. After completion of the reaction, the resultant was neutralized with acetic acid to a pH of about 7, and subjected to liquid removal, drying, and pulverization, thereby obtaining a carboxymethyl cellulose sodium salt having a degree of carboxymethyl substitution of 0.24 and a degree of crystallization of cellulose type I of 73%. The rate of effective utilization of the carboxymethylating agent was 29%. The methods for measuring the degree of carboxymethyl substitution and the degree of crystallization of cellulose type I, and the method for calculating the rate of effective utilization of the carboxymethylating agent are as described above.

(Production Example 5)

A carboxymethyl cellulose sodium salt was obtained in the same manner as in Production Example 4 except that the concentration of IPA in the reaction liquid in the carboxymethylation reaction was 50% by the change in amount of IPA added. The degree of carboxymethyl substitution was 0.31, the degree of crystallization of cellulose type I was 66%, and the rate of effective utilization of the carboxymethylating agent was 37%.

(Production Example 6)

A carboxymethyl cellulose sodium salt was obtained in the same manner as in Production Example 1 except that the concentration of IPA in the reaction liquid in the carboxymethylation reaction was 65% by the change in amount of IPA added. The degree of carboxymethyl substitution was 0.20, the degree of crystallization of cellulose type I was 74%, and the rate of effective utilization of the carboxymethylating agent was 25%.

(Comparative Production Example 3)

A carboxymethyl cellulose sodium salt was obtained in the same manner as in Production Example 4 except that a solution of 45 parts of sodium hydroxide in 100 parts of water was used in the mercerization reaction, instead of the solution of 20 parts of sodium hydroxide in 100 parts of water, the solvent in the carboxymethylation reaction was 100% water, and 150 parts of sodium monochloroacetate was used as the carboxymethylating agent, instead of 60 parts of sodium monochloroacetate. The degree of carboxymethyl substitution was 0.28, the degree of crystallization of cellulose type I was 45%, and the rate of effective utilization of the carboxymethylating agent was 13%.

(Comparative Production Example 4)

A carboxymethyl cellulose sodium salt was obtained in the same manner as in Production Example 4 except that dissolving pulp (manufactured by Nippon Paper Industries Co., Ltd., NDPS) was used instead of the hardwood pulp, a solution of 500 parts of IPA and 48 parts of sodium hydroxide in 100 parts of water was used in the mercerization reaction, and a solution of 37 parts of monochloroacetic acid in 45 parts of 90% IPA was used in the carboxymethylation reaction. The degree of carboxymethyl substitution was 0.50, the degree of crystallization of cellulose type I was 43%, and the rate of effective utilization of the carboxymethylating agent was 78.8%.

Each carboxymethyl cellulose of Production Examples 4 to 6 was subjected to measurements of the proportion of the filtration residue, the Schopper-Riegler freeness, the Canadian standard freeness, the amount of drainage, and the degree of anionization, according to the above methods. The results are shown in Table 5.

TABLE 5

| | | Production Example 4 | Production Example 5 | Production Example 6 |
|---|---|---|---|---|
| Solvent in mercerization | Water | 100% | 100% | 100% |
| | Organic solvent | — | — | — |
| Solvent in carboxymethylation | Water | 70% | 50% | 35% |
| | Organic solvent | IPA 30% | IPA 50% | IPA 65% |
| Rate of effective utilization of carboxymethylating agent | | 29% | 37% | 25% |
| Degree of carboxymethyl substitution | | 0.24 | 0.31 | 0.20 |
| Degree of crystallization of cellulose type I | | 73% | 66% | 74% |
| Proportion of filtration residue | | 7% | 2% | 3% |
| Schopper-Riegler freeness (°SR) | | 66.7 | 71.3 | Not measured |
| Canadian standard freeness (ml) | | 106 | 85 | Not measured |
| Amount of drainage (ml/10 seconds) | | 369 | 302 | Not measured |
| Degree of anionization (meq/g) | | 0.32 | 0.53 | Not measured |

Examples 13 to 15, and Comparative Examples 9 and 10 Breads

Each dough of Examples and Comparative Examples was prepared by formulation as represented below. Thereafter, such each resulting dough was fermented and baked according to steps of a usual straight method, thereby obtaining each square bread. Such each resulting bread was sensorily evaluated by ten trained panelists, with respect to the water retention ability after baking. The results are shown in Table 6.

| Formulation of dough for bread | |
|---|---|
| Wheat flour | 100.0 parts |
| Yeast | 2.0 parts |

-continued

| Formulation of dough for bread | |
|---|---|
| Yeast food | 0.05 parts |
| Sugar | 7.0 parts |
| Salt | 2.0 parts |
| Skimmed milk powder | 2.0 parts |
| Shortening | 4.0 parts |
| Each carboxymethyl cellulose salt | 0.5 parts |
| Water | 72.0 parts. |

Sensory Evaluation with Respect to Water Retention Ability

The water retention ability (moist texture (mouthfeel)) of such each resulting bread was evaluated as either good or poor by ten trained panelists. The results are shown in Table 6. The symbols of "Good", "Fair", and "Poor" in Table 6 represent the following evaluation results:
 Good: nine panelists or more out of ten panelists evaluated the water retention ability (moist texture) as good
 Fair: six to eight panelists out of ten panelists evaluated the water retention ability as good
 Poor: five panelists or less out of ten panelists evaluated the water retention ability as good.

Evaluation with Respect to Shape Retention Ability

The shape retention ability of such each resulting bread was determined by measuring the volume with a laser volumeter VM-2000V (Astaix Inc.) before and after heating with a toaster, and the rate of volume reduction was calculated from the resulting value, and rated according to the following criteria:
 Good: the rate of volume reduction after heating with a toaster was 7% or less
 Fair: the rate of volume reduction after heating with a toaster was more than 7% to 9% or less
 Poor: the rate of volume reduction after heating with a toaster was more than 9%.

TABLE 6

| | CMC salt used | Water retention ability (moist texture) | Shape retention ability |
|---|---|---|---|
| Example 13 | Production Example 4 | Good | Good |
| Example 14 | Production Example 5 | Good | Good |
| Example 15 | Production Example 6 | Good | Good |
| Comparative Example 9 | Comparative Production Example 3 | Fair | Poor |
| Comparative Example 10 | Comparative Production Example 4 | Poor | Poor |

As clear from the results in Table 6, it can be seen that the dispersion composition of the present invention imparts a moist texture to a bread and is suitable as an agent imparting water retention ability, for use in food products.

Examples 16 to 18, and Comparative Examples 11 and 12: Gummi Candy

Each gummi candy stock solution of Examples and Comparative Examples was prepared by formulation as represented below. A mold made of PP (length×width×height=20 mm×20 mm×15 mm) was filled with the resulting gummi candy stock solution so that the height was 10 mm. A mesh having a diameter of 20 cm and a height of 6 cm was placed in a pan having a diameter of 24 cm and a height of 14 cm dedicated for an IH heater so that the bottom of the mesh faced upward, and 1 L of water was placed therein. The pan was heated with the IH heater, and the heater was set so as to keep its temperature, when water was boiled and steam started to be generated. The internal temperature of the pan was here 100° C. The mold made of PP, filled with the gummi candy stock solution, was placed on the bottom of the mesh, a lid was closed so that a wet cloth was sandwiched between the pan and the lid, and the resultant was steam-heated for 30 minutes, thereby obtaining each gummi candy. Such each resulting gummi candy was evaluated with respect to textures and sticky feeling. The results are shown in Table 7.

| Formulation of gummi candy stock solution | |
|---|---|
| Reduced starch syrup | 49.4 parts |
| Powder sugar | 42.8 parts |
| Each carboxymethyl cellulose salt | 6.4 parts |
| Citric acid | 1.2 parts |
| Grape flavor | 0.2 parts |

Evaluation of Textures

The mouthfeel textures (firm textures, juiciness) of such each resulting gummi candy were evaluated as either good or poor by ten trained panelists. The results are shown in Table 7. The symbols of "Good", "Fair", and "Poor" in Table 7 represent the following evaluation results:
 Good: nine panelists or more out of ten panelists evaluated the textures as good
 Fair: six to eight panelists out of ten panelists evaluated the textures as good
 Poor: five panelists or less out of ten panelists evaluated the textures as good.

Evaluation of Sticky Feeling

The degree of stickiness was sensorily evaluated by touching such each resulting gummi candy. The criteria are as follows:
 Good: not sticky at all
 Fair: almost not sticky
 Poor: strong sticky feeling.

TABLE 7

| | CMC salt used | Textures (firm textures, juiciness) | Sticky feeling |
|---|---|---|---|
| Example 16 | Production Example 4 | Good | Good |
| Example 17 | Production Example 5 | Good | Good |
| Example 18 | Production Example 6 | Good | Good |
| Comparative Example 11 | Comparative Production Example 3 | Poor | Good |
| Comparative Example 12 | Comparative Production Example 4 | Poor | Poor |

It has been found from the results in Table 7 that the dispersion composition of the present invention can impart firm resilience to a gummi candy and is suitable as an agent imparting shape retention ability, for use in food products. It has also been found that such each additive not only imparts a juicy texture, but also is hardly sticky, and is suitable as an agent imparting water retention ability, for use in food products.

(Examples 19 to 21, and Comparative Examples 13 and 14: Probiotic Drinks)

Each carboxymethyl cellulose sodium salt was added to granulated sugar and 70% isomerized liquid sugar, in a predetermined amount calculated so that the following formulation was achieved, and water was added thereto for complete dissolution. The dissolved liquid was sterilized at 80° C. for 10 minutes and cooled to 20° C.±1° C., thereafter a predetermined amount of fermented milk was added thereto, and the resultant was mixed and stirred. The resultant was allowed to pass through a homogenizer at 150 kg/cm² once. The mixed and stirred liquid homogenized was sterilized at 90° C. and then cooled to 20° C., and 2.0 ml of 7% sodium benzoate was further added for corruption prevention, thereby obtaining each probiotic drink of Examples and Comparative Examples. Such each resulting drink was evaluated with respect to textures and dispersion stability. The results are shown in Table 8.

| Formulation of probiotic drink | |
| --- | --- |
| Fermented milk (on anhydrous basis) | 3.0 parts |
| Granulated sugar | 1.5 parts |
| 70% Isomerized liquid sugar | 9.3 parts |
| Each carboxymethyl cellulose salt | 0.5 parts |
| Water | 85.7 parts |

Evaluation of Textures

The mouthfeel textures (smoothness, less gooeyness and clump) of such each resulting probiotic drink were evaluated as either good or poor by ten trained panelists. The results are shown in Table 8. The symbols of "Good", "Fair", and "Poor" in Table 8 represent the following evaluation results:
  Good: nine panelists or more out of ten panelists evaluated the textures as good
  Fair: six to eight panelists out of ten panelists evaluated the textures as good
  Poor: five panelists or less out of ten panelists evaluated the textures as good.

Evaluation of Dispersion Stability

Such each resulting probiotic drink was placed in a 100-ml measuring cylinder and left to still stand for 2 weeks, and the amount of precipitation of milk protein in such a cylindrical tube after 2 weeks was read. It was indicated that, as the value was smaller, the stability of such each probiotic drink was more excellent. The criteria are as follows:
  Good: the amount of precipitation was less than 5.0 ml
  Fair: the amount of precipitation was 5.0 ml or more and less than 8.0 ml
  Poor: the amount of precipitation was 8.0 ml or more.

TABLE 8

| | CMC salt used | Textures (smoothness, less gooeyness and clump) | Dispersion stability |
| --- | --- | --- | --- |
| Example 19 | Production Example 4 | Good | Good |
| Example 20 | Production Example 5 | Good | Good |
| Example 21 | Production Example 6 | Good | Good |
| Comparative Example 13 | Comparative Production Example 3 | Fair | Poor |
| Comparative Example 14 | Comparative Production Example 4 | Poor | Fair |

It has been found from the results in Table 8 that the dispersion composition of the present invention is excellent in dispersion stabilization of a probiotic drink, and is suitable as a dispersion stabilizer for use in food products. It has also been found that such any additive has smoothness to the throat and is less in gooeyness and clump, and can be used as a viscosity modifier for use in food products, which is less in gooeyness.

(Examples 22 to 24, and Comparative Examples 15 and 16: Chocolate Beverage)

A cocoa powder, sugar, a skimmed milk powder, and each carboxymethyl cellulose sodium salt were added in predetermined amounts calculated so that the following formulation was achieved, water was added thereto, and the resultant was heated up to 80° C. with stirring by a homomixer and thus preliminarily emulsified, and homogenized by a homogenizer at a pressure of 300 kgf/cm². Thereafter, a can was filled therewith, and the resultant was sterilized at 121° C. for 30 minutes, thereby obtaining each chocolate beverage of Examples and Comparative Examples. Such each resulting chocolate beverage was evaluated with respect to textures and dispersion stability. The results are shown in Table 9.

| Formulation of chocolate beverage | |
| --- | --- |
| Cocoa powder | 4.0 parts |
| Sugar | 10.0 parts |
| Skimmed milk powder | 4.0 parts |
| Each carboxymethyl cellulose salt | 2.0 parts |
| Water | 80.0 parts |

Evaluation of Textures

The mouthfeel textures (smoothness, low roughness) of such each resulting chocolate beverage were evaluated as either good or poor by ten trained panelists. The results are shown in Table 9. The symbols of "Good", "Fair", and "Poor" in Table 9 represent the following evaluation results:
  Good: nine panelists or more out of ten panelists evaluated the textures as good
  Fair: six to eight panelists out of ten panelists evaluated the textures as good
  Poor: five panelists or less out of ten panelists evaluated the textures as good.

Evaluation of Dispersion Stability

Such each resulting chocolate beverage was placed in a 100-ml graduated cylinder and left to still stand for 2 weeks, and the amount of precipitation of milk protein in such a cylindrical tube after 2 weeks was read. It was indicated that, as the value was smaller, the stability of such each chocolate beverage was more excellent. The criteria are as follows:
  Good: the amount of precipitation was less than 5.0 ml
  Fair: the amount of precipitation was 5.0 ml or more and less than 8.0 ml
  Poor: the amount of precipitation was 8.0 ml or more

TABLE 9

| | CMC salt used | Textures (smoothness, low roughness) | Dispersion stability |
| --- | --- | --- | --- |
| Example 22 | Production Example 4 | Good | Good |
| Example 23 | Production Example 5 | Good | Good |
| Example 24 | Production Example 6 | Good | Good |
| Comparative Example 15 | Comparative Production Example 3 | Fair | Poor |
| Comparative Example 16 | Comparative Production Example 4 | Poor | Fair |

It has been found from the results in Table 9 that the dispersion composition of the present invention is excellent in dispersion stabilization of a chocolate beverage, can impart a smooth texture low in roughness, to a beverage, and is suitable as a dispersion stabilizer for use in food products.

Examples 25 to 27, and Comparative Examples 17 and 18: Dispersion Stability of Cocoa Powder The dispersion stability was visually observed in a case where 5 parts of each carboxymethyl cellulose sodium salt was added to 100 parts of an aqueous 20% solution of commercially available powder cocoa (manufactured by Morinaga & Co., Ltd.). Further, after still standing for 24 hours, re-stirring was made and the re-dispersibility was visually observed. Both dispersion stability and re-dispersibility were evaluated as follows: a case where no precipitate was observed on the bottom of a storage container was rated as "Good", a case where a precipitate was slightly observed on a portion of the bottom of a storage container was rated as "Fair", and a case where a precipitate was observed entirely on the bottom of a storage container was rated as "Poor". The results are shown in Table 10.

TABLE 10

|  | CMC salt used | Dispersion stability | Re-dispersibility |
|---|---|---|---|
| Example 25 | Production Example 4 | Good | Good |
| Example 26 | Production Example 5 | Good | Good |
| Example 27 | Production Example 6 | Good | Good |
| Comparative Example 17 | Comparative Production Example 3 | Poor | Poor |
| Comparative Example 18 | Comparative Production Example 4 | Fair | Fair |

It has been found from the results in Table 10 that the dispersion composition of the present invention is excellent in dispersion stabilization and re-dispersibility of a cocoa beverage, and is suitable as a dispersion stabilizer for use in food products.

(Examples 28 to 30, and Comparative Examples 19 and 20: Pudding)

A powdery mixture of raw materials other than a pudding flavor, formulated as represented below, was added with water and fresh cream being stirred, the resultant was stirred and dissolved at 80° C. for 10 minutes, thereafter the pudding flavor was added thereto, a container was filled therewith, and the resultant was cooled, thereby adjusting each pudding of Examples and Comparative Examples. Thereafter, the shape retention ability and texture of such each pudding taken out from the container were evaluated. The results are shown in Table 11.

| Formulation of pudding | |
|---|---|
| Fresh cream | 5.0 parts |
| Sugar | 10.0 parts |
| Skimmed milk powder | 8.0 parts |
| Carboxymethyl cellulose salt | 0.3 parts |
| Pudding flavor | 0.1 parts |
| Water | 77.0 parts |

Evaluation of Texture

The mouthfeel texture (smoothness) of such each resulting pudding was evaluated as either good or poor by ten trained panelists. The results are shown in Table 11. The symbols of "Good", "Fair", and "Poor" in Table 11 represent the following evaluation results:
Good: nine panelists or more out of ten panelists evaluated the texture as good
Fair: six to eight panelists out of ten panelists evaluated the texture as good
Poor: five panelists or less out of ten panelists evaluated the texture as good.

Evaluation of Shape Retention Ability

Such each resulting pudding was taken out from the container, and whether or not the shape collapsed was visually evaluated according to the following criteria.
Good: the same shape as that of the container was almost kept
Poor: the shape significantly collapsed under its own weight.

TABLE 11

|  | CMC salt used | Texture (smoothness) | Shape retention ability |
|---|---|---|---|
| Example 28 | Production Example 4 | Good | Good |
| Example 29 | Production Example 5 | Good | Good |
| Example 30 | Production Example 6 | Good | Good |
| Comparative Example 19 | Comparative Production Example 3 | Fair | Poor |
| Comparative Example 20 | Comparative Production Example 4 | Poor | Poor |

It has been found from the results in Table 11 that the dispersion composition of the present invention not only imparts sufficient shape retention ability to a pudding, but also is kept in smooth texture, and is suitable as an emulsion stabilizer and an agent imparting shape retention ability, for use in food products.

(Examples 31 to 33, and Comparative Examples 21 and 22: Jelly)

A powdery mixture of sugar, each carboxymethyl cellulose sodium salt, trisodium citrate, and calcium lactate formulated as represented below was added with water being stirred, the resultant was heated, stirred, and dissolved at 80° C. for 10 minutes, thereafter citric acid (anhydrous) was added thereto, the resultant was stirred and mixed, the total amount of the resulting mixture was corrected by water, a container was filled with the mixture, and the mixture was sterilized at 85° C. for 30 minutes and solidified by water cooling, thereby producing each jelly of Examples and Comparative Examples. Thereafter, the shape retention ability and textures of such each jelly taken out from the container were evaluated. The results are shown in Table 12.

| Formulation of jelly | |
|---|---|
| Sugar | 15.0 parts |
| Citric acid | 0.2 parts |
| Each carboxymethyl cellulose salt | 0.3 parts |
| Trisodium citrate | 0.2 parts |
| Calcium lactate | 0.2 parts |
| Water | 84.0 parts |

Evaluation of Textures

The mouthfeel textures (proper resilience, juiciness) of such each resulting jelly were evaluated as either good or poor by ten trained panelists. The results are shown in Table 12. The symbols of "Good", "Fair", and "Poor" in Table 12 represent the following evaluation results:
Good: nine panelists or more out of ten panelists evaluated the textures as good
Fair: six to eight panelists out of ten panelists evaluated the textures as good
Poor: five panelists or less out of ten panelists evaluated the textures as good.

Evaluation of Shape Retention Ability

Such each resulting jelly was taken out from the container, and whether or not the shape collapsed was visually evaluated according to the following criteria.

Good: the same shape as that of the container was almost maintained

Poor: the shape significantly collapsed under its own weight.

TABLE 12

|  | CMC salt used | Textures (proper resilience, juiciness) | Shape retention ability |
|---|---|---|---|
| Example 31 | Production Example 4 | Good | Good |
| Example 32 | Production Example 5 | Good | Good |
| Example 33 | Production Example 6 | Good | Good |
| Comparative Example 21 | Comparative Production Example 3 | Poor | Poor |
| Comparative Example 22 | Comparative Production Example 4 | Poor | Poor |

It has been found from the results in Table 12 that the dispersion composition of the present invention can impart to each jelly, not only sufficient shape retention ability and proper resilience, but also a juicy texture, and is suitable as an agent imparting shape retention ability and an agent imparting water retention ability, for use in food products.

(Examples 34 to 36, and Comparative Examples 23 and 24: Hamburger Steak)

After comminuted meat, an onion, breadcrumbs, an egg, black pepper, common salt, and water formulated as represented below were mixed by an SK mixer for 3 minutes, each carboxymethyl cellulose sodium salt was added thereto and well mixed, and 100 g of each oval shaped article was formed. Such each resulting hamburger steak was cooked in a pan so that both surfaces of the hamburger steak were on high heat for 2 minutes and thereafter were on low heat with a lid for 12 minutes in total, thereby adjusting each hamburger steak of Examples and Comparative Examples. The shape retention ability and textures of such each resulting hamburger steak were evaluated. The results are shown in Table 13.

| Formulation of hamburger steak | |
|---|---|
| Comminuted meat | 57.9 parts |
| Onion | 21.1 parts |
| Breadcrumbs | 10.5 parts |
| Egg | 6.3 parts |
| Black pepper | 0.1 parts |
| Common salt | 0.8 parts |
| Each carboxymethyl cellulose salt | 0.5 parts |
| Water | 3.2 parts |

Evaluation of Textures

The mouthfeel textures (proper firmness, smoothness) of such each resulting hamburger steak were evaluated as either good or poor by ten trained panelists. The results are shown in Table 13. The symbols of "Good", "Fair", and "Poor" in Table 13 represent the following evaluation results:

Good: nine panelists or more out of ten panelists evaluated the textures as good Fair: six to eight panelists out of ten panelists evaluated the textures as good Poor: five panelists or less out of ten panelists evaluated the textures as good.

Evaluation of Shape Retention Ability

The shape retention ability of such each hamburger steak during cooking was evaluated according to the following criteria.

Good: the shape hardly collapsed

Poor: the shape easily collapsed.

TABLE 13

|  | CMC salt used | Textures (proper firmness, smoothness) | Shape retention ability |
|---|---|---|---|
| Example 34 | Production Example 4 | Good | Good |
| Example 35 | Production Example 5 | Good | Good |
| Example 36 | Production Example 6 | Good | Good |
| Comparative Example 23 | Comparative Production Example 3 | Fair | Poor |
| Comparative Example 24 | Comparative Production Example 4 | Poor | Poor |

It has been found from the results in Table 13 that the dispersion composition of the present invention can impart sufficient shape retention ability and also favorable textures to a hamburger steak, and is suitable as, for example, an agent imparting shape retention ability, for use in food products.

Examples 37 to 39, and Comparative Examples 25 and 26: Textures of Pancake and Bread Milk and an egg were added to a commercially available pancake mix (Pancake Mix manufactured by Nippon Flour Mills Co., Ltd.), 1% by weight of each carboxymethyl cellulose sodium salt was added thereto, the resultant was baked on a hot plate (160° C., 5 minutes) 5 minutes later, and the moist feeling of each pancake was evaluated by ten panelists immediately after such cooking and after 20 hours of such cooking.

Common salt, sugar, milk, an egg, butter, and dry yeast were added to commercially available bread flour (brand: Nisshin *Camellia*), 1% by weight of each carboxymethyl cellulose sodium salt was added thereto, each bread roll was produced according to an ordinary method, and the moist feeling of such each bread roll was evaluated by ten panelists immediately after such production and after 20 hours of such production.

The results are shown in Table 14. The symbols of "Good", "Fair", and "Poor" in Table 14 represent the following evaluation results:

Good: nine panelists or more out of ten panelists evaluated the texture (moist texture, mouthfeel) as good Fair: six to eight panelists out of ten panelists evaluated the texture as good Poor: five panelists or less out of ten panelists evaluated the texture as good.

TABLE 14

|  |  | Pancake | | Bread roll | |
|---|---|---|---|---|---|
|  | CMC salt used | Immediate aftermath | After 20 hours | Immediate aftermath | After 20 hours |
| Example 37 | Production Example 4 | Good | Good | Good | Good |
| Example 38 | Production Example 5 | Good | Good | Good | Good |
| Example 39 | Production Example 6 | Good | Good | Good | Good |

TABLE 14-continued

| | | Pancake | | Bread roll | |
|---|---|---|---|---|---|
| | CMC salt used | Immediate aftermath | After 20 hours | Immediate aftermath | After 20 hours |
| Comparative Example 25 | Comparative Production Example 3 | Fair | Poor | Fair | Poor |
| Comparative Example 26 | Comparative Production Example 4 | Fair | Poor | Poor | Poor |

It has been found from the results in Table 14 that the dispersion composition of the present invention can impart a moist texture to a pancake and/or a bread roll over a long time, and is suitable as, for example, an agent imparting water retention ability, for use in food products.

(Examples 40 to 42, and Comparative Examples 27 and 28: Milky Lotion (Cosmetic Product))

Each milky lotion (cosmetic product) of Examples and Comparative Examples was produced by formulation as represented below. Such each resulting milky lotion was evaluated with respect to emulsion stability, non-rough feeling, non-sticky feeling, spreadability, moisture retention ability, and attachment ability. The results are shown in Table 15.

| Formulation of milky lotion | |
|---|---|
| Stearic acid | 4.0 parts |
| Squalane | 5.0 parts |
| Glycerin | 5.0 parts |
| Propylene glycol | 5.0 parts |
| Sucrose fatty acid ester | 2.0 parts |
| Each carboxymethyl cellulose salt | 3.0 parts |
| Water | 70.0 parts |

Evaluation of Emulsion Stability

Such each milky lotion was left to still stand at room temperature for 1 week, and a case where no precipitate was observed on the bottom of a storage container was rated as "Good" and a case where any precipitate was observed thereon was rated as "Poor".

Evaluation of Non-Rough Feeling, Non-Sticky Feeling, Spreadability, Moisture Retention Ability, and Attachment Ability The non-rough feeling, non-sticky feeling, spreadability, moisture retention ability, and attachment ability of such each resulting milky lotion were evaluated as either good or poor by fifteen trained female panelists. The results are shown in Table 15. The symbols of "Good", "Fair", and "Poor" in Table 15 represent the following evaluation results:

Good: eleven panelists or more out of fifteen panelists evaluated such properties as good Fair: six to ten panelists out of fifteen panelists evaluated such properties as good Poor: five panelists or less out of fifteen panelists evaluated such properties as good.

TABLE 15

| | CMC salt used | Non-rough feeling | Non-sticky feeling | Spreadability | Moisture retention ability | Attachment ability |
|---|---|---|---|---|---|---|
| Example 40 | Production Example 4 | Good | Good | Good | Good | Good |
| Example 41 | Production Example 5 | Good | Good | Good | Good | Good |
| Example 42 | Production Example 6 | Good | Good | Good | Good | Good |
| Comparative Example 27 | Comparative Production Example 3 | Poor | Fair | Poor | Poor | Poor |
| Comparative Example 28 | Comparative Production Example 4 | Poor | Poor | Poor | Fair | Fair |

It has been found from the results in Table 15 that the dispersion composition of the present invention imparts not only emulsion stability, and low-rough feeling and low-sticky feeling, but also spreadability, moisture retention ability, and favorable attachment ability, to each milky lotion, and is suitable as an emulsion stabilizer, an agent imparting water retention ability, and a viscosity modifier, which are for use in cosmetic products.

The invention claimed is:

1. A method for producing a dispersion composition, comprising
    step 1 of preparing a mixture comprising a carboxymethyl cellulose having a degree of carboxymethyl substitution of 0.20 or more and having a degree of crystallization of cellulose type I of 50% or more, and a water-based medium, and
    step 2 of subjecting the mixture obtained in step 1 to stirring at a rotational speed of 8000 to 15000 rpm for 1 minute or more, thereby obtaining a dispersion composition, wherein
    the carboxymethyl cellulose in the dispersion composition has a median diameter of 10.0 to 150.0 μm; and
    wherein the dispersion composition has a viscosity (6 rpm, 25° C.) of 1000 mPa·s to 30000 mPa·s at a solid content of the carboxymethyl cellulose of 1% (w/v).

2. The production method according to claim 1, wherein a median diameter $D_{50A}$ of the carboxymethyl cellulose before the stirring in step 2 and a median diameter $D_{50B}$ of the carboxymethyl cellulose after the stirring in step 2 satisfy the following expression:

$$90 \leq D_{50B}/D_{50A} \times 100 \leq 110.$$

3. The production method according to claim 1, wherein the dispersion composition has a viscosity (60 rpm, 25° C.) of 100 mPa·s to 10000 mPa·s at a solid content of the carboxymethyl cellulose of 1% (w/v).

4. The production method according to claim 1, wherein the step 1 comprises:
   adding a mercerizing agent to a cellulose in a solvent containing mainly water to prepare a mercerized cellulose, and
   adding a carboxymethylating agent to the mercerized cellulose in a mixed solvent of water and an organic solvent to prepare the carboxymethyl cellulose.

* * * * *